United States Patent
Joo et al.

(10) Patent No.: US 9,254,251 B2
(45) Date of Patent: Feb. 9, 2016

(54) BENZOIC ACID AMIDE COMPOUND

(75) Inventors: Yung Hyup Joo, Yongin-si (KR); Heung Soo Baek, Yongin-si (KR); Chang Seok Lee, Yongin-si (KR); Soo Jeong Choi, Yongin-si (KR); Ho Sik Rho, Yongin-si (KR); Mi Young Park, Yongin-si (KR); Song Seok Shin, Yongin-si (KR); Kyung Min Lim, Yongin-si (KR); Young Ho Park, Yongin-si (KR)

(73) Assignee: AMOREPACIFIC CORPORATION (KR)

( * ) Notice: Subject to any disclaimer, the term of this patent is extended or adjusted under 35 U.S.C. 154(b) by 43 days.

(21) Appl. No.: 14/126,329

(22) PCT Filed: Aug. 3, 2012

(86) PCT No.: PCT/KR2012/006200
§ 371 (c)(1),
(2), (4) Date: Dec. 13, 2013

(87) PCT Pub. No.: WO2013/022236
PCT Pub. Date: Feb. 14, 2013

(65) Prior Publication Data
US 2014/0234241 A1    Aug. 21, 2014

(30) Foreign Application Priority Data

Aug. 5, 2011 (KR) .................. 10-2011-0078309

(51) Int. Cl.
A61K 8/00 (2006.01)
A61Q 19/02 (2006.01)
A61K 8/42 (2006.01)
A61Q 19/00 (2006.01)
C07C 235/46 (2006.01)
C07C 235/48 (2006.01)
A61K 8/06 (2006.01)

(52) U.S. Cl.
CPC . *A61K 8/42* (2013.01); *A61Q 19/00* (2013.01); *A61Q 19/02* (2013.01); *C07C 235/46* (2013.01); *C07C 235/48* (2013.01)

(58) Field of Classification Search
None
See application file for complete search history.

(56) References Cited

U.S. PATENT DOCUMENTS

| 5,786,379 A | 7/1998 | Bernardon |
| 2008/0214675 A1 | 9/2008 | Ley et al. |

FOREIGN PATENT DOCUMENTS

| EP | 2412701 | 2/2012 |
| JP | 08-143525 | 6/1996 |
| JP | 2011-140447 | 7/2011 |
| KR | 10-2007-0046577 | 5/2007 |
| KR | 100726280 | 6/2007 |
| KR | 10-2008-0014279 | 2/2008 |

OTHER PUBLICATIONS

Baek. Bioorganic & Medicinal Chemistry Letters 22 (2012) 2110-2113.*
European Search Report-EP12822128.0 dated Feb. 18, 2015, citing enumerated references listed below.
Ho Sik Rho, et al., "Ester Derivatives of Kojic Acid and Polyphenols Containing Adamantane Moiety with Tyrosinase Inhibitory and Anti-inflammatory Properties", Bull. Korean Chem. Soc., vol. 32, No. 4, pp. 1411-1414, 2011.
Ho Sik Rho, et al., "Studies on depigmenting activities of dihydroxyl benzamide derivatives containing adamantane moiety", Bioorganic & Medicinal Chemistry Letters, vol. 19, pp. 1532-1533, 2009.
Written Opinion—PCT/KR2012/006200 dated Feb. 13, 2013.
International Search Report—PCT/KR2012/006200 dated Feb. 13, 2013.

* cited by examiner

*Primary Examiner* — Robert C Hayes
*Assistant Examiner* — Lori K Mattison
(74) *Attorney, Agent, or Firm* — Cantor Colburn LLP

(57) ABSTRACT

The present invention relates to a novel benzoic acid amide derivative compound, isomers thereof, pharmaceutically acceptable salts thereof, prodrugs thereof, hydrates thereof, or solvates thereof. The novel compound has excellent skin whitening effects.

13 Claims, No Drawings

BENZOIC ACID AMIDE COMPOUND

TECHNICAL FIELD

The present disclosure relates to a novel benzamide compound.

BACKGROUND ART

Melanin protects skin organs beneath the dermis by blocking UV at the epidermis and also protects the skin by scavenging free radicals. Also, melanin is the primary determinant of skin color and is the cause of pigmentation such as freckles, dark spots, etc. when existing in excess.

Melanin is produced by melanocytes, which are found in the basal layer of the epidermis. It is known that the production of melanin is promoted by stimuli such as UV or inflammation. Accordingly, the melanin production can be reduced by decreasing external stimulation, blocking signal transduction or inhibiting synthesis of the melanin-producing enzyme tyrosinase or inhibiting activity thereof.

Until now, kojic acid, hydroquinone, arbutin, azelaic acid, aloesin, 4-butylresorcinol, resveratrol, ceramide, sphingosine-1-phosphate, sphingosylphosphorylcholline, etc. are known to be able to regulate melanin production by promoting tyrosinase breakdown or regulating glycosylation. However, these substances are not used widely due to unsatisfactory skin whitening effect and stability as well as skin irritation. Accordingly, development of a substance that provides superior skin whitening effect with less side effects is necessary.

DISCLOSURE

Technical Problem

The present disclosure is directed to providing a novel benzamide derivative compound. The present disclosure is also directed to providing a composition containing a benzamide derivative compound exhibiting skin whitening effect.

Technical Solution

In a general aspect, there is provided a compound of Chemical Formula 1, an isomer thereof, a pharmaceutically acceptable salt thereof, a prodrug thereof, a hydrate thereof or a solvate thereof:

[Chemical Formula 1]

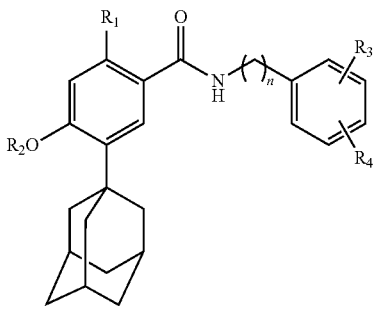

Wherein each of $R_1$, $R_3$ and $R_4$ is independently selected from a group consisting of hydrogen, hydroxy, $C_1$-$C_5$ alkoxy, $C_3$-$C_6$ cycloalkoxy, aryloxy and $C_1$-$C_5$ haloalkoxy;

$R_2$ is selected from a group consisting of hydrogen, $C_1$-$C_5$ alkyl, $C_3$-$C_6$ cycloalkyl, aryl and $C_1$-$C_5$ haloalkyl; and n is an integer selected from 1 to 5.

In another general aspect, there is provided a composition for skin whitening, containing the compound of Chemical Formula 1, the isomer thereof, the pharmaceutically acceptable salt thereof, the prodrug thereof, the hydrate thereof or the solvate thereof.

Advantageous Effects

A novel compound, an isomer thereof, a pharmaceutically acceptable salt thereof, a prodrug thereof, a hydrate thereof or a solvate thereof according to the present disclosure has superior skin whitening effect by reducing melanin production and inhibiting the activity of tyrosinase.

Best Mode

In order to develop substances exhibiting improved skin whitening effect while having less side effects, the inventors of the present disclosure have synthesized polyhydroxybenzamide derivative compounds having kazinol as a backbone structure. Among them, the compounds having adamantane substituents have been found to exhibit superior effect of reducing melanin production and inhibiting tyrosinase activity. The superior effect of reducing melanin production and inhibiting tyrosinase activity may be attributable to increased absorption owing to increased oleophilicity provided by the adamantane group.

DEFINITION

As used herein, "skin" refers to the tissue that covers the body surface of an animal, including not only the face or body but also the scalp and hair, in the broadest concept.

As used herein, "alkyl" refers to a monovalent saturated aliphatic hydrocarbon chain. The hydrocarbon chain may be either straight or branched. In an exemplary embodiment of the present disclosure, the "alkyl" may have 1-5 carbon atoms ("$C_1$-$C_5$ alkyl"). In another exemplary embodiment, it may have 1-4 carbon atoms ("$C_1$-$C_4$ alkyl"). In another exemplary embodiment, it may have 1-3 carbon atoms ("$C_1$-$C_3$ alkyl"). Specifically, the "alkyl" includes methyl, ethyl, n-propyl, isopropyl, n-butyl, isobutyl, tert-butyl or t-amyl, but is not limited thereto.

As used herein, "alkoxy" refers to an —OR group, where R is an alkyl group defined above. Specifically, the "alkoxy" includes methoxy, ethoxy, n-propoxy, isopropoxy, n-butoxy, tert-butoxy, sec-butoxy, n-pentoxy or 1,2-dimethylbutoxy, but is not limited thereto.

As used herein, "cycloalkyl" refers to a cyclic saturated aliphatic hydrocarbon group. The number following C means the number of carbon atoms that form a ring. For example, "$C_3$-$C_6$ cycloalkyl" refers to cycloalkyl having 3-6 ring-forming carbon atoms. In an exemplary embodiment of the present disclosure, examples of the "cycloalkyl" include cyclopropyl, cyclobutyl, cyclopentyl or cyclohexyl, but are not limited thereto. In another exemplary embodiment of the present disclosure, the "cycloalkyl" group may be substituted with one or more alkyl group, for example, with a $C_1$-$C_6$ alkyl group, specifically with a $C_1$-$C_3$ alkyl group, more specifically with a methyl group. If the "cycloalkyl" has more than one substituent, the substituents may be identical or different.

As used herein, "cycloalkoxy" refers to an —OR group, where R is a "cycloalkyl" group defined above.

As used herein, "halo" or "halogen" includes fluoro, chloro, bromo or iodo. In an exemplary embodiment of the present disclosure, the halo group may be fluoro or chloro.

As used herein, "haloalkyl" refers to an "alkyl" group defined above which is substituted with one or more identical (e.g., trifluoromethyl or pentafluoroethyl) or different halogen.

As used herein, "aryl" refers to an aromatic hydrocarbon radical. The "aryl" group may be, for example, phenyl, naphthyl, indenyl, azulenyl or anthracenyl, specifically phenyl.

As used herein, "hydroxy" refers to an —OH radical.

As used herein, "isomer" includes not only optical isomers (e.g., essentially pure enantiomers, essentially pure diastereomers or mixtures thereof) but also conformation isomers (i.e., isomers different only in angles of one or more chemical bonds), constitutional isomers (especially, tautomers) or geometric isomers (i.e., cis-trans isomers).

As used herein, "essentially pure" means, for example, when used in connection with enantiomers or diastereomers, that the specific compound as an example of the enantiomer or the diastereomer is present in about 90% (w/w) or more, specifically about 95% or more, more specifically about 97% or more or about 98% or more, further more specifically about 99% or more, even more specifically about 99.5% or more.

As used herein, "pharmaceutically acceptable" means approved by a regulatory agency of the government or an international organization or listed in the Pharmacopoeia or other generally recognized pharmacopoeia for use in animals, more specifically in humans, since significant toxic effect can be avoided when used with a common medicinal dosage.

As used herein, "pharmaceutically acceptable salt" refers to a salt which is pharmaceutically acceptable and exhibits the desired pharmacological activity of its parent compound. The salt may be (1) an acid addition salt formed from an inorganic acid such as hydrochloric acid, hydrobromic acid, sulfuric acid, nitric acid, phosphoric acid, etc., or an organic acid such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid or muconic acid or (2) a salt formed as an acidic proton present in the parent compound is replaced.

As used herein, "prodrug" refers to a drug whose physical and chemical properties have been changed such that it does not exhibit physiological activity as it is but exerts medicinal effect after it is converted to the original drug through chemical or enzymatic action in vivo.

As used herein, "hydrate" refers to a compound bound with water. It is used in a broad sense, including an inclusion compound which lacks chemical bonding with water.

As used herein, "solvate" refers to a higher-order compound formed between a solute molecule or ion, and a solvent molecule or ion.

DETAILED DESCRIPTION

In an aspect, the present disclosure provides a compound of Chemical Formula 1, an isomer thereof, a pharmaceutically acceptable salt thereof, a prodrug thereof, a hydrate thereof or a solvate thereof:

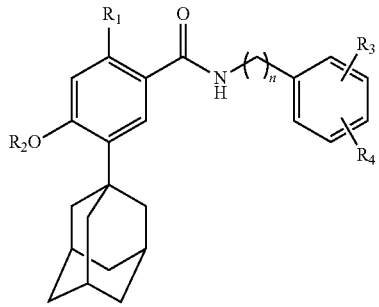

[Chemical Formula 1]

Wherein each of $R_1$, $R_3$ and $R_4$ is independently selected from a group consisting of hydrogen, hydroxy, $C_1$-$C_3$ alkoxy, $C_3$-$C_6$ cycloalkoxy, aryloxy and $C_1$-$C_3$ haloalkoxy;

$R_2$ is selected from a group consisting of hydrogen, $C_1$-$C_3$ alkyl, $C_3$-$C_6$ cycloalkyl, aryl and $C_1$-$C_3$ haloalkyl; and n is an integer selected from 1 to 3.

In an exemplary embodiment of the present disclosure, each of $R_1$, $R_3$ and $R_4$ may be independently selected from a group consisting of hydrogen, hydroxy and $C_1$-$C_3$ alkoxy, $R_2$ may be hydrogen or $C_1$-$C_3$ alkyl and n may be 1 or 2.

In another exemplary embodiment of the present disclosure, the compound, the isomer thereof, the pharmaceutically acceptable salt thereof, the prodrug thereof, the hydrate thereof or the solvate thereof may be selected from a group consisting of 5-adamantan-1-yl-N-[2-(3,4-dihydroxyphenyl)-ethyl]-2,4-dihydroxybenzamide, 5-adamantan-1-yl-N-[2-(3,4-dihydroxyphenyl)-ethyl]-2-hydroxy-4-methoxybenzamide 5-adamantan-1-yl-N-(3,4-dihydroxybenzyl)-2,4-dihydroxybenzamide, 5-adamantan-1-yl-N-(3,4-dihydroxybenzyl)-2-hydroxy-4-methoxybenzamide, 5-adamantan-1-yl-2,4-dihydroxy-N-[2-(4-hydroxyphenyl)-ethyl]benzamide, 5-adamantan-1-yl-2-hydroxy-N-[2-(4-hydroxyphenyl)-ethyl]-4-methoxybenzamide, 5-adamantan-1-yl-N-[2-(4-hydroxyphenyl)-ethyl]-2,4-dimethoxybenzamide, 5-adamantan-1-yl-N-(2,4-dihydroxybenzyl)-2,4-dihydroxybenzamide, 5-adamantan-1-yl-N-(2,4-dihydroxybenzyl)-2-hydroxy-4-methoxybenzamide, 5-adamantan-1-yl-N-(2,4-dihydroxybenzyl)-2,4-dimethoxybenzamide, 3-adamantan-1-yl-N-(3,4-dihydroxybenzyl)-4-hydroxybenzamide, 3-adamantan-1-yl-N-(3,4-dihydroxybenzyl)-4-methoxybenzamide, 3-adamantan-1-yl-N-[2-(3,4-dihydroxyphenyl)-ethyl]-4-hydroxybenzamide, 3-adamantan-1-yl-N-[2-(3,4-dihydroxyphenyl)-ethyl]-4-methoxybenzamide, 3-adamantan-1-yl-4-hydroxy-N-[2-(4-hydroxyphenyl)-ethyl]benzamide, 3-adamantan-1-yl-N-[2-(4-hydroxyphenyl)-ethyl]-4-methoxybenzamide, 3-adamantan-1-yl-N-(2,4-dihydroxybenzyl)-4-hydroxybenzamide, 3-adamantan-1-yl-N-(2,4-dihydroxybenzyl)-4-methoxybenzamide, 5-adamantan-1-yl-N-(2,5-dimethoxybenzyl)-2,4-dihydroxybenzamide, 5-adamantan-1-yl-N-(2,5-dihydroxybenzyl)-2,4-dihydroxybenzamide, 5-adamantan-1-yl-N-(3,5-dimethoxybenzyl)-2,4-dihydroxybenzamide and 5-adamantan-1-yl-2,4-dihydroxy-N-(3-hydroxy-5-methoxybenzyl)benzamide.

In another aspect, the present disclosure provides a method for preparing the adamantane-substituted benzamide compound, including:

i) synthesizing adamantanyl hydroxybenzoic acid by reacting hydroxybenzoic acid with adamantane compound in the presence of an acid catalyst;

ii) synthesizing adamantanyl alkoxybenzoic acid by reacting the adamantanyl hydroxybenzoic acid with alkyl sulfate; and iii) synthesizing the adamantane-substituted benzamide compound by reacting the adamantanyl alkoxybenzoic acid with hydroxy-substituted alkylphenylamine.

The method for preparing the adamantane-substituted benzamide compound according to the present disclosure may be represented by Scheme 1.

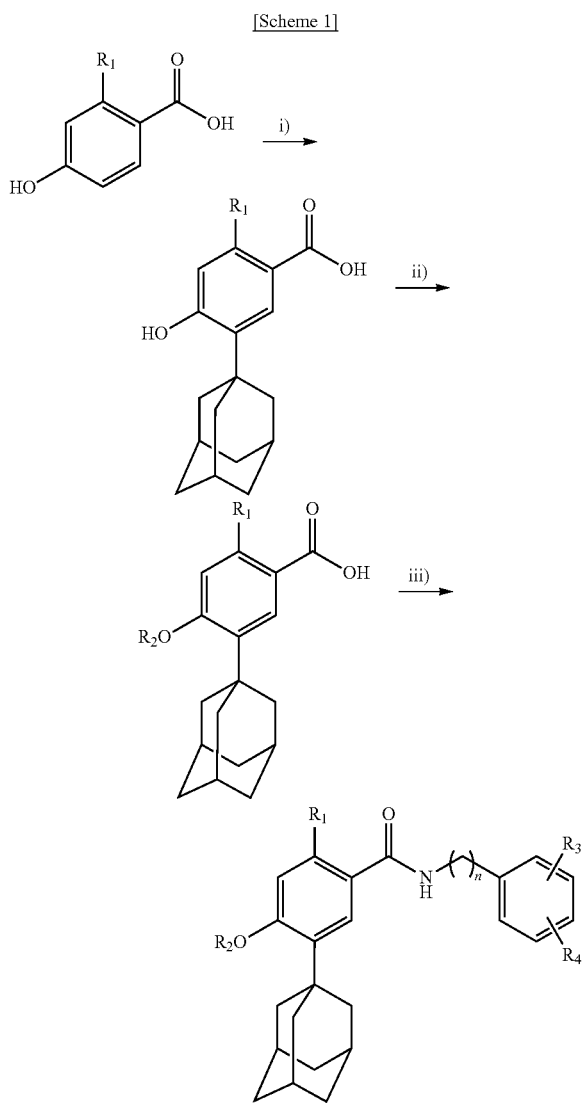

In Scheme 1, each of $R_1$, $R_3$ and $R_4$ is independently selected from a group consisting of hydrogen, hydroxy, $C_1$-$C_5$ alkoxy, $C_3$-$C_6$ cycloalkoxy, aryloxy and $C_1$-$C_5$ haloalkoxy;

$R_2$ is selected from a group consisting of hydrogen, $C_1$-$C_5$ alkyl, $C_3$-$C_6$ cycloalkyl, aryl and $C_1$-$C_5$ haloalkyl; and n is an integer selected from 1 to 5.

In another aspect, the present disclosure provides a method for preparing the adamantane-substituted benzamide compound, including:

i) synthesizing adamantanyl dihydroxybenzoic acid by reacting dihydroxybenzoic acid with adamantane compound in the presence of an acid catalyst;

ii) synthesizing adamantanyl hydroxyalkoxybenzoic acid or adamantanyl dialkoxybenzoic acid by reacting the adamantanyl dihydroxybenzoic acid with dialkyl sulfate in the presence of hydroxide; and iii) synthesizing the adamantane-substituted benzamide compound by reacting the adamantanyl hydroxyalkoxybenzoic acid or adamantanyl dialkoxybenzoic acid with hydroxy-substituted benzylamine or phenethylamine.

In another aspect, the present disclosure provides a method for preparing the adamantane-substituted benzamide compound, including:

i) synthesizing 5-adamantanyl-2,4-dihydroxybenzoic acid by reacting 2,4-dihydroxybenzoic acid with 1-adamantanol at room temperature in a dichloromethane solvent in the presence of acetic acid and sulfuric acid catalysts;

ii) synthesizing 5-adamantanyl-2-hydroxy-4-methoxybenzoic acid or 5-adamantanyl-2,4-dimethoxybenzoic acid by reacting the 5-adamantanyl-2,4-dihydroxybenzoic acid with dimethyl sulfate in the presence of sodium hydroxide or potassium hydroxide; and iii) synthesizing the adamantane-substituted benzamide compound by reacting the 5-adamantanyl-2-hydroxy-4-methoxybenzoic acid or 5-adamantanyl-2,4-dimethoxybenzoic acid with hydroxy-substituted benzylamine or phenethylamine in the presence of N-hydroxysuccinimide (HOSu) or N,N'-dicyclohexylcarbodiimide (DCC).

In another aspect, the present disclosure provides a composition for skin whitening containing the compound, the isomer thereof, the pharmaceutically acceptable salt thereof, the prodrug thereof, the hydrate thereof or the solvate thereof as an active ingredient. The compound, the isomer thereof, the pharmaceutically acceptable salt thereof, the prodrug thereof, the hydrate thereof or the solvate thereof may exhibit superior skin whitening effect by reducing melanin production and inhibiting tyrosinase activity.

In an exemplary embodiment, the composition according to the present disclosure may contain the compound, the isomer thereof, the pharmaceutically acceptable salt thereof, the prodrug thereof, the hydrate thereof or the solvate thereof in an amount of 0.01-20 wt %, specifically 0.1-10 wt %, more specifically 0.5-5 wt %, based on the total weight of the composition. When the active ingredient is contained in the above-described amount, the effect desired by the present disclosure can be achieved adequately while satisfying stability and safety of the composition and cost effectiveness. Specifically, if the compound, the isomer thereof, the pharmaceutically acceptable salt thereof, the prodrug thereof, the hydrate thereof or the solvate thereof is contained in an amount less than 0.01 wt %, skin whitening effect may be insufficient. And, if it is contained in an amount exceeding 20 wt %, cost effectiveness may be not good.

In another aspect, the present disclosure provides a composition for external application to skin, containing the compound, the isomer thereof, the pharmaceutically acceptable salt thereof, the prodrug thereof, the hydrate thereof or the solvate thereof as an active ingredient. In another aspect, the present disclosure provides a cosmetic composition containing the compound, the isomer thereof, the pharmaceutically acceptable salt thereof, the prodrug thereof, the hydrate thereof or the solvate thereof as an active ingredient. The cosmetic composition may exhibit superior skin whitening effect and, specifically, may improve or prevent freckles, dark spots or pigmentation.

The composition according to the present disclosure may be provided as any formulation suitable for topical application. For example, it may be provided in the form of solution, oil-in-water emulsion, water-in-oil emulsion, suspension, solid, gel, powder, paste, foam or aerosol. These formulations may be prepared by a method commonly employed in the art.

The composition according to the present disclosure may further contain other ingredients that may provide synergic effect without negatively affecting the desired effect. Specifically, the composition according to the present disclosure may further contain arbutin or ascorbic acid derivatives that can enhance skin whitening effect. Also, the composition according to the present disclosure may further contain moisturizer, emollient, surfactant, UV absorbent, antiseptic, fungicide, antioxidant, pH adjuster, organic or inorganic pigment, flavor, cooling agent or antiperspirant. The content of these ingredients may be determined within ranges not negatively affecting the purpose and effect of the present disclosure by those skilled in the art. The content of these ingredients may be 0.01-5 wt %, specifically 0.01-3 wt %, based on the total weight of the composition.

In another aspect, the present disclosure provides a pharmaceutical composition containing the compound, the isomer thereof, the pharmaceutically acceptable salt thereof, the prodrug thereof, the hydrate thereof or the solvate thereof as an active ingredient. The pharmaceutical composition may exhibit excellent skin whitening effect and, specifically, may improve or prevent freckles, dark spots or pigmentation.

The pharmaceutical composition according to the present disclosure may be administered orally or parenterally, rectally, topically, transdermally, intravenously, intramuscularly, intraperitoneally or subcutaneously. Formulations for oral administration may be in the form of tablet, pill, soft and hard capsule, granule, powder, fine granule, liquid, emulsion or pellet, but are not limited thereto. Formulations for parenteral administration may be in the form of solution, suspension, emulsion, gel, injection, medicinal drip, suppository, patch or spray, but are not limited thereto. These formulations may be prepared easily by a method commonly employed in the art and surfactant, vehicle, hydrating agent, emulsification accelerator, suspension, salt or buffer for osmotic pressure control, colorant, flavor, stabilizer, antiseptic, preservative or other commonly used adjuvants may be used adequately.

The administration dosage of the active ingredient will vary depending on the age, gender and body weight of a subject, pathological condition and severity thereof, administration route and discretion of a diagnoser. Determination of the administration dosage considering these factors is in the level of those skilled in the art. A daily dosage may be, for example, 0.1-100 mg/kg/day, more specifically 5-50 mg/kg/day, but is not limited thereto.

MODE FOR INVENTION

Hereinafter, the present disclosure will be described in detail through examples and test examples. However, the following examples and test examples are for illustrative purposes only and it will be apparent to those of ordinary skill in the art that the scope of the present disclosure is not limited thereby.

EXAMPLE 1

Preparation of 5-adamantan-1-yl-N-[2-(3,4-dihydroxyphenyl)-ethyl]-2,4-dihydroxybenzamide

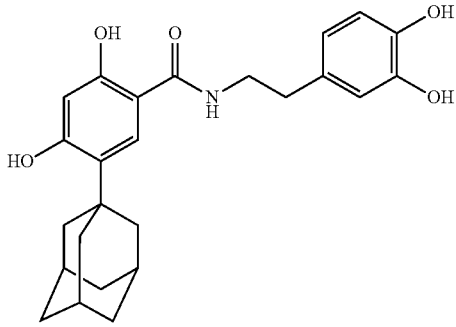 [SMILES: O=C(NCCc1ccc(O)c(O)c1)c1cc(C23CC4CC(CC(C4)C2)C3)c(O)cc1O]

(1) Preparation of 5-adamantan-1-yl-2,4-dihydroxybenzoic acid 2,4-Dihydroxybenzoic acid (9.24 g) and 1-adamantanol (9.14 g) are dissolved in dichloromethane (200 mL) and then stirred. After adding acetic acid (17.1 mL) mixed with concentrated sulfuric acid (3.3 mL) dropwise, the mixture is stirred at room temperature for 12 hours. After adding water (200 mL), sodium bicarbonate is added until the pH of the solution becomes 6. The produced solid is filtered to obtain 8.82 g of 5-adamantan-1-yl-2,4-dihydroxybenzoic acid as solid of a light color.

$^1$H NMR (300 MHz, DMSO-$d_6$) 12.40 (brs, 1H), 10.17 (s, 1H), 7.47 (s, 1H), 6.27 (s, 1H), 2.00 (s, 9H), 1.70 (s, 6H).

(2) Preparation of 5-adamantan-1-yl-N-[2-(3,4-dihydroxyphenyl)-ethyl]-2,4-dihydroxybenzamide 5-Adamantan-1-yl-2,4-dihydroxybenzoic acid (0.606 g) obtained in (1), N-hydroxysuccinimide (0.24 g) and N,N'-dicyclohexylcarbodiimide (0.43 g) are dissolved in dioxane (10 mL) and then stirred for 12 hours. The produced solid is filtered and the filtrate is added dropwise to a mixture solution of dopamine bromate (0.54 g), sodium bicarbonate (0.18 g) and water (2 mL). After stirring at 50° C. for 2 hours, the solution is cooled to room temperature, neutralized with 10% HCl solution and washed with ethyl acetate (50 mL). The organic layer is dried with anhydrous magnesium sulfate, filtered, concentrated under reduced pressure and separated by column chromatography to obtain 0.2 g of the target compound as white solid.

$^1$H NMR (300 MHz, DMSO-$d_6$) 12.63 (s, 1H), 9.90 (s, 1H), 8.74 (s, 1H), 8.63 (s, 1H), 8.58 (m, 1H), 7.38 (m, 1H), 6.63 (m, 2H), 6.47 (d, 1H, J=7.5 Hz), 6.25 (s, 1H), 3.32 (m, 2H), 2.63 (t, 2H, J=7.2 Hz), 2.03 (s, 9H), 1.72 (s, 6H).

EXAMPLE 2

Preparation of 5-adamantan-1-yl-N-[2-(3,4-dihydroxyphenyl)-ethyl]-2-hydroxy-4-methoxybenzamide

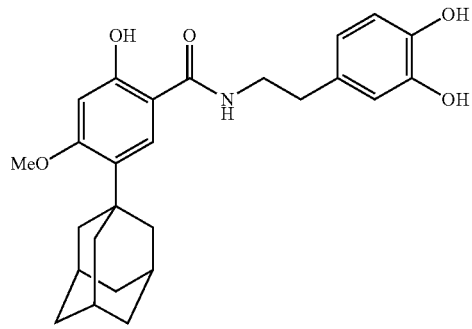 [SMILES: COc1cc(O)c(C(=O)NCCc2ccc(O)c(O)c2)cc1C12CC3CC(CC(C3)C1)C2]

0.12 g of the target compound is obtained as white solid in substantially the same manner as in (2) of Example 1, except for using 5-adamantan-1-yl-2-hydroxy-4-methoxybenzoic acid instead of 5-adamantan-1-yl-2,4-dihydroxybenzoic acid.

$^1$H NMR (300 MHz, DMSO-$d_6$) 12.89 (s, 1H), 8.76 (s, 1H), 8.70 (m, 1H), 8.65 (s, 1H), 7.43 (s, 1H), 6.62 (m, 2H), 6.45 (m, 2H), 3.79 (s, 3H), 3.36 (m, 2H), 2.64 (t, 2H, J=7.2 Hz), 2.01 (s, 9H), 1.72 (s, 6H).

EXAMPLE 3

Preparation of 5-adamantan-1-yl-N-(3,4-dihydroxybenzyl)-2,4-dihydroxybenzamide

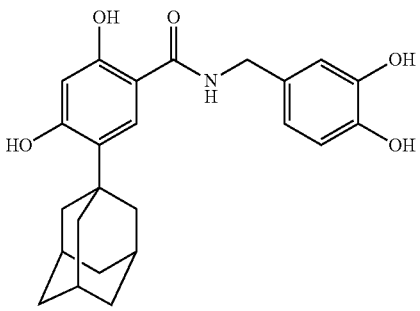 [SMILES: O=C(NCc1ccc(O)c(O)c1)c1cc(C23CC4CC(CC(C4)C2)C3)c(O)cc1O]

0.09 g of the target compound is obtained as white solid in substantially the same manner as in (2) of Example 1, except for using 3,4-dihydroxybenzylamine instead of dopamine.

$^1$H NMR (300 MHz, DMSO-d$_6$) 12.74 (s, 1H), 9.95 (s, 1H), 8.98 (m, 1H), 8.85 (s, 1H), 8.71 (s, 1H), 7.44 (s, 1H), 6.67 (m, 2H), 6.56 (d, 1H, J=7.8 Hz), 6.26 (s, 1H), 4.28 (d, 2H, J=5.4 Hz), 2.03 (s, 9H), 1.71 (s, 6H).

EXAMPLE 4

Preparation of 5-adamantan-1-yl-N-(3,4-dihydroxybenzyl)-2-hydroxy-4-methoxybenzamide

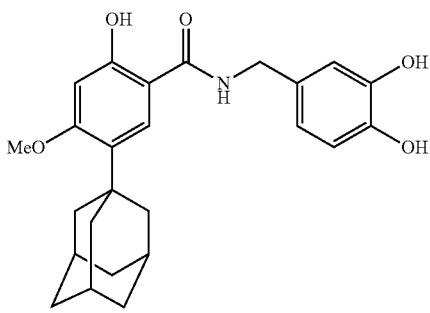 [SMILES: COc1cc(O)c(C(=O)NCc2ccc(O)c(O)c2)cc1C12CC3CC(CC(C3)C1)C2]

0.17 g of the target compound is obtained as white solid in substantially the same manner as in (2) of Example 1, except for using 5-adamantan-1-yl-2-hydroxy-4-methoxybenzoic acid instead of 5-adamantan-1-yl-2,4-dihydroxybenzoic acid and using 3,4-dihydroxybenzylamine instead of dopamine.

$^1$H NMR (300 MHz, DMSO-d$_6$) 12.99 (s, 1H), 9.09 (m, 1H), 8.85 (s, 1H), 8.72 (s, 1H), 7.48 (s, 1H), 6.67 (m, 2H), 6.57 (d, 1H, J=8.1 Hz), 6.43 (s, 1H), 4.30 (d, 2H, J=5.4 Hz), 3.79 (s, 3H), 2.00 (s, 9H), 1.71 (s, 6H).

EXAMPLE 5

Preparation of 5-adamantan-1-yl-2,4-dihydroxy-N-[2-(4-hydroxyphenyl)-ethyl]benzamide

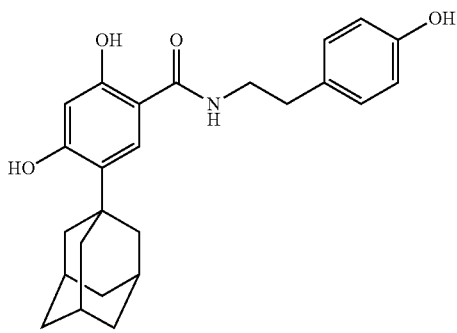 [SMILES: O=C(NCCc1ccc(O)cc1)c1cc(C23CC4CC(CC(C4)C2)C3)c(O)cc1O]

0.2 g of the target compound is obtained as white solid in substantially the same manner as in (2) of Example 1, except for using tyramine instead of dopamine.

$^1$H NMR (300 MHz, DMSO-d$_6$) 12.59 (s, 1H), 9.91 (s, 1H), 9.16 (s, 1H), 8.60 (s, 1H), 7.38 (s, 1H), 7.02 (d, 2H, J=8.1 Hz), 6.68 (d, 2H, J=8.1 Hz), 6.25 (s, 1H), 3.37 (m, 2H), 2.70 (t, 2H, J=7.2 Hz), 2.03 (s, 9H), 1.72 (s, 6H).

EXAMPLE 6

Preparation of 5-adamantan-1-yl-2-hydroxy-N-[2-(4-hydroxyphenyl)-ethyl]-4-methoxybenzamide

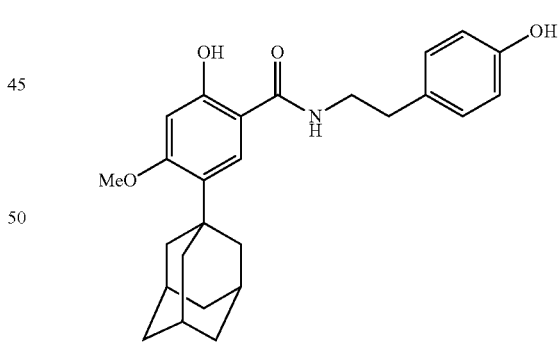

0.15 g of the target compound is obtained as solid of a light color in substantially the same manner as in (2) of Example 1, except for using 5-adamantan-1-yl-2-hydroxy-4-methoxybenzoic acid instead of 5-adamantan-1-yl-2,4-dihydroxybenzoic acid and using tyramine instead of dopamine.

$^1$H NMR (300 MHz, DMSO-d$_6$) 12.85 (s, 1H), 9.17 (s, 1H), 8.70 (m, 1H), 7.42 (s, 1H), 7.02 (d, 2H, J=8.1 Hz), 6.68 (d, 2H, J=8.1 Hz), 6.41 (s, 1H), 3.78 (s, 3H), 3.39 (m, 2H), 2.71 (m, 2H), 2.00 (s, 9H), 1.72 (s, 6H).

EXAMPLE 7

Preparation of 5-adamantan-1-yl-N-[2-(4-hydroxyphenyl)-ethyl]-2,4-dimethoxybenzamide

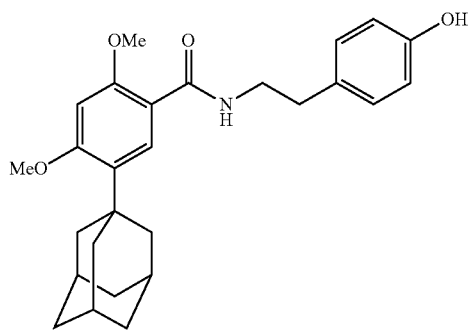 [SMILES: COc1cc(OC)c(C23CC4CC(CC(C4)C2)C3)cc1C(=O)NCCc1ccc(O)cc1]

5-Adamantan-1-yl-2,4-dimethoxybenzoic acid (0.32 g) is dissolved in dichloromethane (5 mL). After adding thionyl chloride (0.08 mL), followed by refluxing for 3 hours, the mixture is cooled to room temperature and concentrated under reduced pressure. Then, 0.28 g of the target compound is obtained as white plate-shaped solid in substantially the same manner as in (2) of Example 1, except for using tyramine instead of dopamine.

$^1$H NMR (300 MHz, DMSO-$d_6$) 9.20 (s, 1H), 7.94 (m, 1H), 7.73 (s, 1H), 7.04 (d, 2H, J=8.1 Hz), 6.70 (d, 2H, J=8.1 Hz), 6.63 (s, 1H), 3.87 (s, 3H), 3.84 (s, 3H), 3.44 (m, 2H), 2.69 (t, 2H, J=7.1 Hz), 1.99 (s, 9H), 1.71 (s, 6H).

EXAMPLE 8

Preparation of 5-adamantan-1-yl-N-(2,4-dihydroxybenzyl)-2,4-dihydroxybenzamide

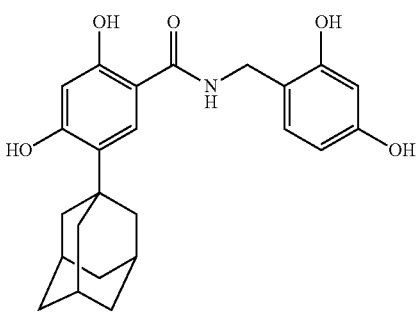 [SMILES: O=C(NCc1ccc(O)cc1O)c1cc(C23CC4CC(CC(C4)C2)C3)c(O)cc1O]

0.24 g of the target compound is obtained as white solid in substantially the same manner as in (2) of Example 1, except for using 2,4-dihydroxybenzylamine instead of dopamine.

$^1$H NMR (300 MHz, DMSO-$d_6$) 12.41 (s, 1H), 9.91 (s, 1H), 9.40 (s, 1H), 9.09 (s, 1H), 8.83 (m, 1H), 7.47 (s, 1H), 6.89 (d, 1H, J=8.1 Hz), 6.26 (s, 2H), 6.16 (d, 1H, J=8.1 Hz), 4.29 (m, 2H), 2.02 (s, 9H), 1.70 (s, 6H).

EXAMPLE 9

Preparation of 5-adamantan-1-yl-N-(2,4-dihydroxybenzyl)-2-hydroxy-4-methoxybenzamide

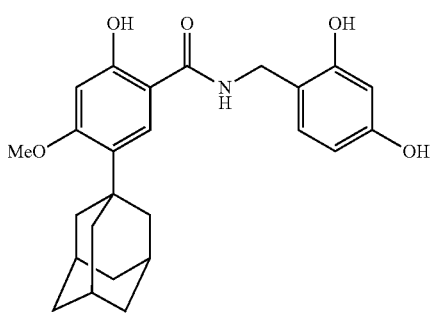 [SMILES: COc1cc(O)c(C(=O)NCc2ccc(O)cc2O)cc1C12CC3CC(CC(C3)C1)C2]

0.14 g of the target compound is obtained as solid of a light color in substantially the same manner as in (2) of Example 1, except for using 5-adamantan-1-yl-2-hydroxy-4-methoxybenzoic acid instead of 5-adamantan-1-yl-2,4-dihydroxybenzoic acid and using 2,4-dihydroxybenzylamine instead of dopamine.

$^1$H NMR (300 MHz, DMSO-$d_6$) 12.73 (s, 1H), 9.40 (s, 1H), 9.11 (s, 1H), 8.95 (m, 1H), 7.52 (s, 1H), 6.90 (d, 1H, J=8.4 Hz), 6.43 (s, 1H), 6.28 (s, 1H), 6.17 (d, 1H, J=8.4 Hz), 4.31 (d, 2H, J=5.4 Hz), 3.79 (s, 3H), 2.00 (s, 9H), 1.71 (s, 6H).

EXAMPLE 10

Preparation of 5-adamantan-1-yl-N-(2,4-dihydroxybenzyl)-2,4-dimethoxybenzamide

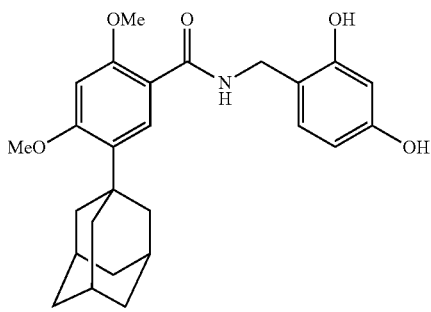 [SMILES: COc1cc(OC)c(C23CC4CC(CC(C4)C2)C3)cc1C(=O)NCc1ccc(O)cc1O]

0.03 g of the target compound is obtained as white solid in substantially the same manner as in (2) of Example 1, except for using 5-adamantan-1-yl-2,4-dimethoxybenzoic acid instead of 5-adamantan-1-yl-2,4-dihydroxybenzoic acid and using 2,4-dihydroxybenzylamine instead of dopamine.

$^1$H NMR (300 MHz, DMSO-$d_6$) 9.67 (s, 1H), 9.13 (s, 1H), 8.51 (m, 1H), 7.78 (m, 1H), 6.92 (d, 1H, J=8.1 Hz), 6.66 (s, 1H), 6.27 (s, 1H), 6.16 (d, 1H, J=8.1 Hz), 4.30 (d, 2H, J=5.4 Hz), 3.93 (s, 3H), 3.88 (s, 3H), 1.98 (s, 9H), 1.71 (s, 6H).

EXAMPLE 11

Preparation of 3-adamantan-1-yl-N-(3,4-dihydroxybenzyl)-4-hydroxybenzamide

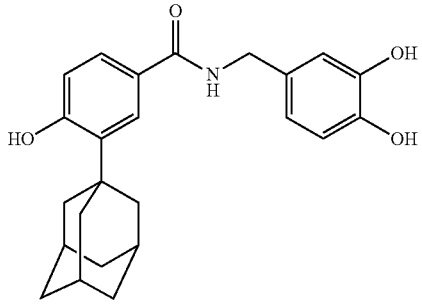 [SMILES: O=C(NCc1ccc(O)c(O)c1)c1ccc(O)c(C23CC4CC(CC(C4)C2)C3)c1]

3-Adamantan-1-yl-4-hydroxybenzoic acid (0.286 g), N-hydroxysuccinimide (0.12 g) and N,N'-dicyclohexylcarbodiimide (0.22 g) are dissolved in dioxane (5 mL) and stirred for 12 hours. The produced solid is filtered and the filtrate is added dropwise to a mixture solution of 3,4-dihydroxybenzylamine bromate (0.25 g), sodium bicarbonate (0.09 g) and water (1 mL). After stirring at 50° C. for 2 hours, the solution is cooled to room temperature, neutralized with 10% HCl solution and washed with ethyl acetate (30 mL). The organic layer is dried with anhydrous magnesium sulfate, filtered, concentrated under reduced pressure and separated by column chromatography to obtain 0.03 g of the target compound as white solid.

$^1$H NMR (300 MHz, DMSO-$d_6$) 9.82 (s, 1H), 8.75 (m, 2H), 8.62 (m, 1H), 7.63 (s, 1H), 7.56 (m, 1H), 6.77 (d, 1H, J=8.4 Hz), 6.69 (s, 1H), 6.64 (d, 1H, J=8.1 Hz), 6.53 (m, 1H), 4.26 (d, 2H, J=6.0 Hz), 2.07 (s, 9H), 1.72 (s, 6H).

EXAMPLE 12

Preparation of 3-adamantan-1-yl-N-(3,4-dihydroxybenzyl)-4-methoxybenzamide

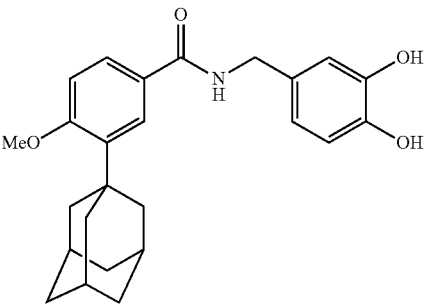 [SMILES: COc1ccc(C(=O)NCc2ccc(O)c(O)c2)cc1C12CC3CC(CC(C3)C1)C2]

0.02 g of the target compound is obtained as solid of a light color in substantially the same manner as in (2) of Example 1, except for using 3-adamantan-1-yl-4-methoxybenzoic acid instead of 5-adamantan-1-yl-2,4-dihydroxybenzoic acid and using 3,4-dihydroxybenzylamine instead of dopamine.

$^1$H NMR (300 MHz, DMSO-$d_6$) 8.74 (m, 3H), 7.75 (d, 1H, J=7.8 Hz), 7.70 (s, 1H), 7.01 (d, 1H, J=8.4 Hz), 6.70 (s, 1H), 6.64 (d, 1H, J=8.1 Hz), 6.54 (d, 1H, J=7.5 Hz), 4.27 (d, 2H, J=6.0 Hz), 3.84 (s, 3H), 2.05 (s, 9H), 1.73 (s, 6H).

EXAMPLE 13

Preparation of 3-adamantan-1-yl-N-[2-(3,4-dihydroxyphenyl)-ethyl]-4-hydroxybenzamide

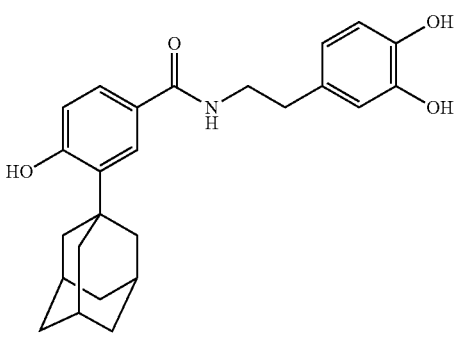 [SMILES: O=C(NCCc1ccc(O)c(O)c1)c1ccc(O)c(C23CC4CC(CC(C4)C2)C3)c1]

0.25 g of the target compound is obtained as white solid in substantially the same manner as in (2) of Example 1, except for using 3-adamantan-1-yl-4-hydroxybenzoic acid instead of 5-adamantan-1-yl-2,4-dihydroxybenzoic acid.

$^1$H NMR (300 MHz, DMSO-$d_6$) 9.78 (s, 1H), 8.71 (brs, 1H), 8.64 (brs, 1H), 8.21 (m, 1H), 7.56 (m, 1H), 7.50 (m, 1H), 6.76 (m, 1H), 6.62 (m, 2H), 6.45 (m, 1H), 3.34 (m, 2H), 2.62 (m, 2H), 2.07 (s, 9H), 1.73 (s, 6H).

EXAMPLE 14

Preparation of 3-adamantan-1-yl-N-[2-(3,4-dihydroxyphenyl)-ethyl]-4-methoxybenzamide

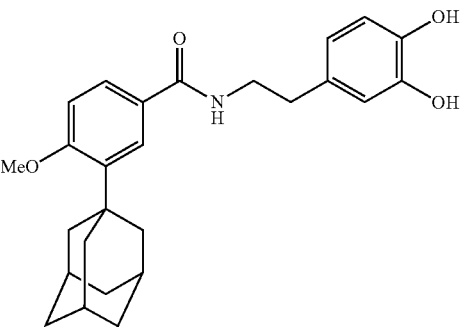 [SMILES: COc1ccc(C(=O)NCCc2ccc(O)c(O)c2)cc1C12CC3CC(CC(C3)C1)C2]

0.19 g of the target compound is obtained as white solid in substantially the same manner as in (2) of Example 1, except for using 3-adamantan-1-yl-4-methoxybenzoic acid instead of 5-adamantan-1-yl-2,4-dihydroxybenzoic acid.

$^1$H NMR (300 MHz, DMSO-$d_6$) 8.73 (brs, 1H), 8.63 (brs, 1H), 8.34 (m, 1H), 7.66 (m, 2H), 7.00 (d, 1H, J=8.7 Hz), 6.63 (m, 2H), 6.46 (d, 1H, J=8.1 Hz), 3.80 (s, 3H), 3.32 (m, 2H), 2.62 (t, 2H, J=8.1 Hz), 2.05 (s, 9H), 1.73 (s, 6H).

EXAMPLE 15

Preparation of 3-adamantan-1-yl-4-hydroxy-N-[2-(4-hydroxyphenyl)-ethyl]benzamide

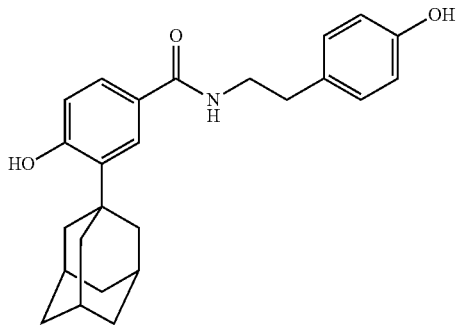 [SMILES: O=C(NCCc1ccc(O)cc1)c1ccc(O)c(C23CC4CC(CC(C4)C2)C3)c1]

0.03 g of the target compound is obtained as white solid in substantially the same manner as in Example 11, except for using tyramine instead of 3,4-dihydroxybenzylamine.

$^1$H NMR (300 MHz, DMSO-$d_6$) 9.78 (s, 1H), 9.14 (s, 1H), 8.33 (m, 1H), 7.56 (d, 1H, J=8.4 Hz), 7.01 (d, 2H, J=8.1 Hz), 6.76 (d, 1H, J=8.4 Hz), 6.67 (d, 2H, J=8.1 Hz), 3.18 (m, 2H), 2.68 (t, 2H, J=7.5 Hz), 2.07 (s, 9H), 1.73 (s, 6H).

EXAMPLE 16

Preparation of 3-adamantan-1-yl-N-[2-(4-hydroxyphenyl)-ethyl]-4-methoxybenzamide

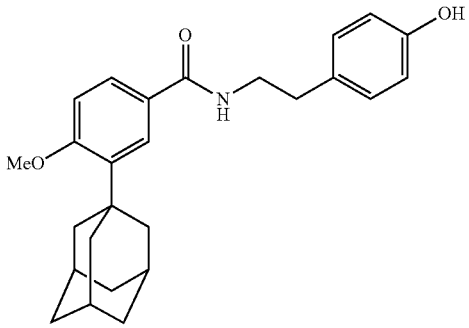 [SMILES: COc1ccc(C(=O)NCCc2ccc(O)cc2)cc1C12CC3CC(CC(C3)C1)C2]

0.03 g of the target compound is obtained as white solid in substantially the same manner as in Example 11, except for using 3-adamantan-1-yl-4-methoxybenzoic acid instead of 3-adamantan-1-yl-4-hydroxybenzoic acid and using tyramine instead of 3,4-dihydroxybenzylamine.

$^1$H NMR (300 MHz, DMSO-$d_6$) 9.14 (s, 1H), 8.33 (t, 1H, J=5.4 Hz), 7.65 (m, 2H), 7.00 (m, 3H), 6.67 (m, 2H), 3.83 (s, 3H), 3.35 (m, 2H), 2.69 (t, 2H, J=7.7 Hz), 2.05 (s, 9H), 1.74 (s, 6H).

EXAMPLE 17

Preparation of 3-adamantan-1-yl-N-(2,4-dihydroxybenzyl)-4-hydroxybenzamide

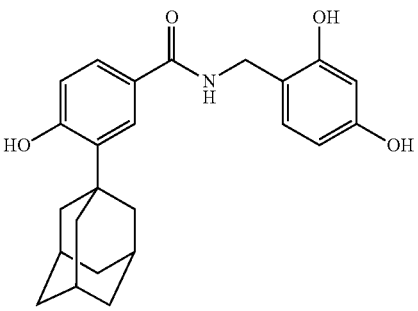 [SMILES: O=C(NCc1ccc(O)cc1O)c1ccc(O)c(C23CC4CC(CC(C4)C2)C3)c1]

0.04 g of the target compound is obtained as white solid in substantially the same manner as in Example 11, except for using 2,4-dihydroxybenzylamine instead of 3,4-dihydroxybenzylamine.

$^1$H NMR (300 MHz, DMSO-$d_6$) 9.87 (s, 1H), 9.64 (s, 1H), 9.09 (s, 1H), 8.73 (m, 1H), 7.58 (m, 2H), 6.89 (d, 1H, J=8.1 Hz), 6.77 (d, 1H, J=7.8 Hz), 6.18 (m, 2H), 4.25 (m, 2H), 2.07 (s, 9H), 1.72 (s, 6H).

EXAMPLE 18

Preparation of 3-adamantan-1-yl-N-(2,4-dihydroxybenzyl)-4-methoxybenzamide

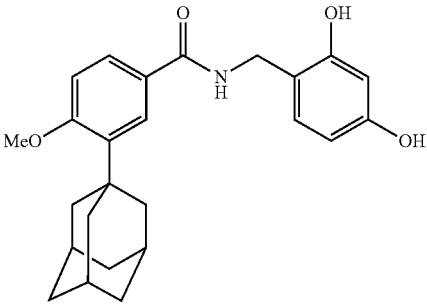 [SMILES: COc1ccc(C(=O)NCc2ccc(O)cc2O)cc1C12CC3CC(CC(C3)C1)C2]

0.03 g of the target compound is obtained as white solid in substantially the same manner as in Example 11, except for using 3-adamantan-1-yl-4-methoxybenzoic acid instead of 3-adamantan-1-yl-4-hydroxybenzoic acid and using 2,4-dihydroxybenzylamine instead of 3,4-dihydroxybenzylamine.

$^1$H NMR (300 MHz, DMSO-$d_6$) 9.58 (s, 1H), 9.09 (s, 1H), 8.81 (t, 1H, J=5.4 Hz), 7.73 (m, 2H), 7.02 (d, 1H, J=8.4 Hz), 6.90 (d, 1H, J=8.1 Hz), 6.18 (m, 2H), 4.26 (d, 2H, J=5.7 Hz), 3.84 (s, 3H), 2.05 (s, 9H), 1.73 (s, 6H).

EXAMPLE 19

Preparation of 5-adamantan-1-yl-N-(2,5-dimethoxy-benzyl)-2,4-dihydroxybenzamide

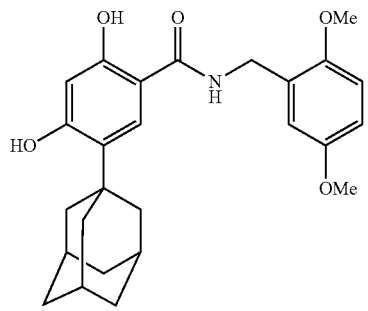 [SMILES: COc1ccc(OC)c(CNC(=O)c2cc(C34CC5CC(CC(C5)C3)C4)c(O)cc2O)c1]

5-Adamantan-1-yl-2,4-dihydroxy-benzoic acid (1.21 g), N-hydroxysuccinimide (0.48 g) and N,N'-dicyclohexylcarbodiimide (0.86 g) are dissolved in dioxane (20 mL) and stirred for 12 hours. The produced solid is filtered and the filtrate is added dropwise to a mixture solution of 2,5-dimethoxybenzylamine (0.77 g), sodium bicarbonate (0.36 g) and water (4 mL). After stirring at 50° C. for 2 hours, the solution is cooled to room temperature, neutralized with 10% HCl solution and washed with ethyl acetate (100 mL). The organic layer is dried with anhydrous magnesium sulfate, concentrated under reduced pressure and separated by column chromatography to obtain 0.43 g of the target compound as white solid.

$^1$H NMR (300 MHz, DMSO-$d_6$) 12.39 (s, 1H), 9.94 (s, 1H), 8.90 (m, 1H), 7.50 (s, 1H), 6.92 (d, 1H, J=8.7 Hz), 6.80 (m, 1H), 6.73 (m, 1H), 6.28 (s, 1H), 4.44 (d, 2H, J=5.7 Hz), 3.77 (s, 3H), 3.65 (s, 3H), 2.04 (s, 9H), 1.71 (s, 6H).

EXAMPLE 20

Preparation of 5-adamantan-1-yl-N-(2,5-dihydroxy-benzyl)-2,4-dihydroxybenzamide

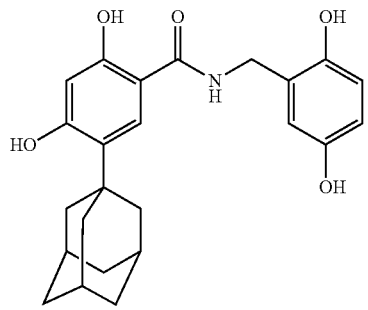 [SMILES: O=C(NCc1cc(O)ccc1O)c1cc(C23CC4CC(CC(C4)C2)C3)c(O)cc1O]

5-Adamantan-1-yl-N-(2,5-dimethoxybenzyl)-2,4-dihydroxybenzamide (0.27 g) is dissolved in dichloromethane (3 mL). After adding BBr$_3$ (1.7 mL in CH$_2$Cl$_2$ 1.0 M solution, 3 eq.) and stirring at room temperature for 2 hours, methanol (5 mL) is added and extraction is carried out using water and dichloromethane. The organic layer is dried with anhydrous magnesium sulfate, filtered, concentrated under reduced pressure and separated by column chromatography to obtain 0.02 g of the target compound as white solid.

$^1$H NMR (300 MHz, DMSO-$d_6$) 12.50 (s, 1H), 9.94 (s, 1H), 8.93 (m, 1H), 8.81 (s, 1H), 8.59 (s, 1H), 7.50 (s, 1H), 6.58 (m, 2H), 6.44 (m, 1H), 6.28 (s, 1H), 4.34 (m, 2H), 2.04 (s, 9H), 1.71 (s, 6H).

EXAMPLE 21

Preparation of 5-adamantan-1-yl-N-(3,5-dimethoxy-benzyl)-2,4-dihydroxybenzamide

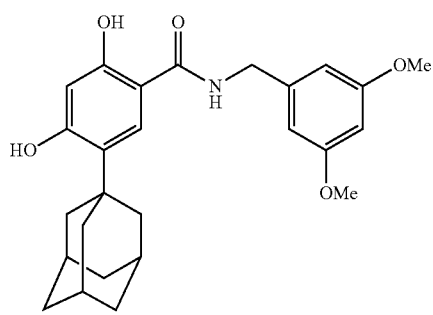 [SMILES: COc1cc(CNC(=O)c2cc(C34CC5CC(CC(C5)C3)C4)c(O)cc2O)cc(OC)c1]

0.31 g of the target compound is obtained as solid of a light color in substantially the same manner as in (2) of Example 1, except for using 3,5-dimethoxybenzylamine instead of dopamine.

$^1$H NMR (300 MHz, DMSO-$d_6$) 12.55 (s, 1H), 9.96 (s, 1H), 9.02 (m, 1H), 7.46 (s, 1H), 6.46 (m, 2H), 6.38 (s, 1H), 6.27 (s, 1H), 4.39 (d, 2H, J=5.4 Hz), 3.71 (s, 6H), 2.04 (s, 9H), 1.71 (s, 6H).

EXAMPLE 22

Preparation of 5-adamantan-1-yl-2,4-dihydroxy-N-(3-hydroxy-5-methoxybenzyl)benzamide

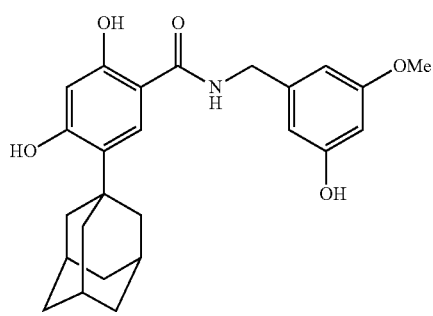 [SMILES: COc1cc(O)cc(CNC(=O)c2cc(C34CC5CC(CC(C5)C3)C4)c(O)cc2O)c1]

5-Adamantan-1-yl-N-(3,5-dimethoxybenzyl)-2,4-dihydroxybenzamide (0.27 g) is dissolved in dichloromethane (3 mL). After adding BBr$_3$ (1.7 mL in CH$_2$Cl$_2$ 1.0 M solution, 3 eq.) and stirring at room temperature for 2 hours, methanol (5 mL) is added and extraction is carried out using water and dichloromethane. The organic layer is dried with anhydrous magnesium sulfate, filtered, concentrated under reduced pressure and separated by column chromatography to obtain 0.045 g of the target compound as white solid.

$^1$H NMR (300 MHz, DMSO-d$_6$) 12.45 (s, 1H), 9.95 (s, 1H), 9.35 (m, 1H), 9.01 (m, 1H), 7.46 (s, 1H), 6.31 (m, 3H), 6.19 (s, 1H), 4.34 (m, 2H), 3.67 (s, 3H), 2.04 (s, 9H), 1.71 (s, 6H).

TEST EXAMPLE 1

Effect of Reducing Melanin Production in Melanocytes

The effect of reducing melanin production of the benzamide derivative compounds prepared in Examples in melanocytes was measured according to the Dooley's method. Mouse-derived B16F10 melanoma cells acquired from the Korean Cell Line Bank were used. DMEM (Cat No. 11995), FBS (Cat No. 16000-044), and antibiotic and antifungal agents (Cat No. 15240-062) necessary for cell culturing were purchased from Invitrogen (GIBCO). The cells were cultured under the condition of 37° C. and 5% CO$_2$. The cultured B16F10 cells were detached using 0.05% trypsin-EDTA and seeded onto a 48-well plate with the same cell number (1×10$^4$ cells/well). From the next day, the culture medium was replaced with one containing 10 ppm of the compound of Examples for three consecutive days. Kojic acid and rucinol were used as positive control. After 5 days, melanin was extracted from the cells by treating with 1 N NaOH at 60° C. for 2 hours, which was quantitated by measuring absorbance at 405 nm. The concentration required to reduce melanin production in melanocytes to half (IC$_{50}$) was calculated and is given in Table 1.

TABLE 1

| Compounds | IC$_{50}$ |
| --- | --- |
| Kojic acid | IC$_{50}$ = 300 μM |
| Rucinol | IC$_{50}$ = 10 μM |
| Example 1 | IC$_{50}$ = 1.2 μM |
| Example 5 | IC$_{50}$ = 1.1 μM |
| Example 8 | IC$_{50}$ = 1.2 μM |
| Example 9 | IC$_{50}$ = 1.8 μM |
| Example 10 | IC$_{50}$ = 1.1 μM |
| Example 12 | IC$_{50}$ = 1.9 μM |
| Example 13 | IC$_{50}$ = 3.0 μM |
| Example 20 | IC$_{50}$ = 2.9 μM |
| Example 21 | IC$_{50}$ = 2.0 μM |

As seen from above, the compounds of Examples can reduce melanin production at much lower concentration as compared to kojic acid and rucinol. Accordingly, it can be seen that the benzamide derivative compounds according to the present disclosure have excellent skin whitening effect by reducing melanin production.

TEST EXAMPLE 2

Effect of Inhibiting Mushroom Tyrosinase Activity

The effect of inhibiting mushroom tyrosinase activity of the benzamide derivative compounds of Examples was measured according to the method of Vanni, et al. Specifically, 49.5 μL of 0.1 M potassium phosphate buffer (pH 6.8), 45 μL of distilled water (DW), 0.5 μL (10 units) of mushroom tyrosinase (SIGMAT-7755) and 5 μL of the benzamide derivative compound of Examples were mixed and reacted at 37° C. for 10 minutes by mixing with 50 μL of 0.3 mg/mL tyrosine aqueous solution in a 96-well plate (total volume: 150 μL). Kojic acid and rucinol were used as positive control. Absorbance of the reaction solution was measured at 480 nm and the concentration required to inhibit tyrosinase activity to 50% (IC$_{50}$) was calculated and is given in Table 2.

TABLE 2

| Compounds | IC$_{50}$ |
| --- | --- |
| Kojic acid | 30 μM |
| Rucinol | 1.3 μM |
| Example 8 | 1.1 μM |
| Example 9 | 0.8 μM |
| Example 10 | 0.9 μM |
| Example 17 | 0.9 μM |
| Example 18 | 1.4 μM |

As seen from above, the benzamide derivative compounds of Examples have excellent effect of inhibiting mushroom tyrosinase activity, even better than kojic acid and rucinol. Accordingly, it can be seen that the benzamide derivative compounds according to the present disclosure have excellent skin whitening effect by inhibiting tyrosinase activity.

Hereinafter, formulation examples of a composition containing the compound, the isomer thereof, the pharmaceutically acceptable salt thereof, the prodrug thereof, the hydrate thereof or the solvate thereof according to the present disclosure will be described in detail. However, the following formulation examples are for illustrative purposes only and it will be apparent to those of ordinary skill in the art that the scope of the present disclosure is not limited thereby.

FORMULATION EXAMPLE 1

Skin Lotion

A lotion is prepared according to a commonly employed method with the composition described in Table 3.

TABLE 3

| Ingredients | Contents (wt %) |
| --- | --- |
| Compound of Example | 0.1 |
| Glycerine | 3.0 |
| Butylene glycol | 2.0 |
| Propylene glycol | 2.0 |
| Carboxyvinyl polymer | 0.1 |
| PEG 12 nonyl phenyl ether | 0.2 |
| Polysorbate 80 | 0.4 |
| Ethanol | 10.0 |
| Triethanolamine | 0.1 |
| Antiseptic, pigment and flavor | adequate |
| Purified water | balance |

FORMULATION EXAMPLE 2

Nourishing Cream

A nourishing cream is prepared according to a commonly employed method with the composition described in Table 4.

TABLE 4

| Ingredients | Contents (wt %) |
| --- | --- |
| Compound of Example | 2.0 |
| Polysorbate 60 | 1.5 |
| Sorbitan sesquioleate | 0.5 |
| PEG 60 hydrogenated castor oil | 2.0 |
| Liquid paraffin | 10.0 |
| Squalane | 5.0 |
| Caprylic/capric triglyceride | 5.0 |

TABLE 4-continued

| Ingredients | Contents (wt %) |
| --- | --- |
| Glycerine | 5.0 |
| Butylene glycol | 3.0 |
| Propylene glycol | 3.0 |
| Triethanolamine | 0.2 |
| Antiseptic, pigment and flavor | adequate |
| Purified water | balance |

FORMULATION EXAMPLE 3

Massage Cream

A massage cream is prepared according to a commonly employed method with the composition described in Table 5.

TABLE 5

| Ingredients | Contents (wt %) |
| --- | --- |
| Compound of Example | 1.0 |
| Beeswax | 10.0 |
| Polysorbate 60 | 1.5 |
| PEG 60 hydrogenated castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerine | 5.0 |
| Butylene glycol | 3.0 |
| Propylene glycol | 3.0 |
| Triethanolamine | 0.2 |
| Antiseptic, pigment and flavor | adequate |
| Purified water | balance |

FORMULATION EXAMPLE 4

Pack

A pack is prepared according to a commonly employed method with the composition described in Table 6.

TABLE 6

| Ingredients | Contents (wt %) |
| --- | --- |
| Compound of Example | 0.2 |
| Polyvinyl alcohol | 13.0 |
| Sodium carboxymethylcellulose | 0.2 |
| Glycerine | 5.0 |
| Allantoin | 0.1 |
| Ethanol | 6.0 |
| PEG 12 nonyl phenyl ether | 0.3 |
| Polysorbate 60 | 0.3 |
| Antiseptic, pigment and flavor | adequate |
| Purified water | balance |

FORMULATION EXAMPLE 5

Gel

A gel is prepared according to a commonly employed method with the composition described in Table 7.

TABLE 7

| Ingredients | Contents (wt %) |
| --- | --- |
| Compound of Example | 0.5 |
| Sodium ethylenediaminetetraacetate | 0.05 |
| Glycerine | 5.0 |
| Carboxyvinyl polymer | 0.3 |
| Ethanol | 5.0 |
| PEG 60 hydrogenated castor oil | 0.5 |
| Triethanolamine | 0.3 |
| Antiseptic, pigment and flavor | adequate |
| Purified water | balance |

FORMULATION EXAMPLE 6

Ointment

An ointment is prepared according to a commonly employed method with the composition described in Table 8.

TABLE 8

| Ingredients | Contents (wt %) |
| --- | --- |
| Compound of Example | 1.5 |
| Glycerine | 8.0 |
| Butylene glycol | 4.0 |
| Liquid paraffin | 15.0 |
| β-Glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Antiseptic, pigment and flavor | adequate |
| Purified water | balance |

The invention claimed is:

1. A compound of Chemical Formula 1, an isomer thereof, a pharmaceutically acceptable salt thereof, a prodrug thereof, a hydrate thereof or a solvate thereof:

[Chemical Formula 1]

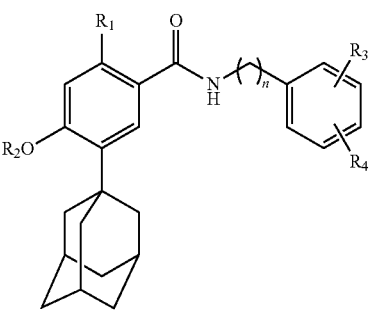

wherein each of $R_1$, $R_3$ and $R_4$ is independently selected from a group consisting of hydrogen, hydroxy, $C_1$-$C_5$ alkoxy, $C_3$-$C_6$ cycloalkoxy, aryloxy and $C_1$-$C_5$ haloalkoxy;

$R_2$ is selected from a group consisting of hydrogen, $C_1$-$C_5$ alkyl, $C_3$-$C_6$ cycloalkyl, aryl and $C_1$-$C_5$ haloalkyl; and n is an integer selected from 1 to 5.

2. The compound, the isomer thereof, the pharmaceutically acceptable salt thereof, the prodrug thereof, the hydrate thereof or the solvate thereof according to claim 1, wherein each of $R_1$, $R_3$ and $R_4$ is independently selected from a group consisting of hydrogen, hydroxy, $C_1$-$C_3$ alkoxy, $C_3$-$C_6$ cycloalkoxy, aryloxy and $C_1$-$C_3$ haloalkoxy;

$R_2$ is selected from a group consisting of hydrogen, $C_1$-$C_3$ alkyl, $C_3$-$C_6$ cycloalkyl, aryl and $C_1$-$C_3$ haloalkyl; and n is an integer selected from 1 to 3.

3. The compound, the isomer thereof, the pharmaceutically acceptable salt thereof, the prodrug thereof, the hydrate thereof or the solvate thereof according to claim 1, wherein the compound is selected from a group consisting of 5-adamantan-1-yl-N-[2-(3,4-dihydroxyphenyl)-ethyl]-2,4-dihydroxybenzamide, 5-adamantan-1-yl-N-[2-(3,4-dihydroxyphenyl)-ethyl]-2-hydroxy-4-methoxybenzamide, 5-adamantan-1-yl-N-(3,4-dihydroxybenzyl)-2,4-dihydroxybenzamide, 5-adamantan-1-yl-N-(3,4-dihydroxybenzyl)-2-hydroxy-4-methoxybenzamide, 5-adamantan-1-yl-2,4-dihydroxy-N-[2-(4-hydroxyphenyl)-ethyl]benzamide, 5-adamantan-1-yl-2-hydroxy-N-[2-(4-hydroxyphenyl)-ethyl]-4-methoxybenzamide, 5-adamantan-1-yl-N-[2-(4-hydroxyphenyl)-ethyl]-2,4-dimethoxybenzamide, 5-adamantan-1-yl-N-(2,4-dihydroxybenzyl)-2,4-dihydroxybenzamide, 5-adamantan-1-yl-N-(2,4-dihydroxybenzyl)-2-hydroxy-4-methoxybenzamide, 5-adamantan-1-yl-N-(2,4-dihydroxybenzyl)-2,4-dimethoxybenzamide, 3-adamantan-1-yl-N-(3,4-dihydroxybenzyl)-4-hydroxybenzamide, 3-adamantan-1-yl-N-(3,4-dihydroxybenzyl)-4-methoxybenzamide, 3-adamantan-1-yl-N-[2-(3,4-dihydroxyphenyl)-ethyl]-4-hydroxybenzamide, 3-adamantan-1-yl-N-[2-(3,4-dihydroxyphenyl)-ethyl]-4-methoxybenzamide, 3-adamantan-1-yl-4-hydroxy-N-[2-(4-hydroxyphenyl)-ethyl]benzamide, 3-adamantan-1-yl-N-[2-(4-hydroxyphenyl)-ethyl]-4-methoxybenzamide, 3-adamantan-1-yl-N-(2,4-dihydroxybenzyl)-4-hydroxybenzamide, 3-adamantan-1-yl-N-(2,4-dihydroxybenzyl)-4-methoxybenzamide, 5-adamantan-1-yl-N-(2,5-dimethoxybenzyl)-2,4-dihydroxybenzamide, 5-adamantan-1-yl-N-(2,5-dihydroxybenzyl)-2,4-dihydroxybenzamide, 5-adamantan-1-yl-N-(3,5-dimethoxybenzyl)-2,4-dihydroxybenzamide and 5-adamantan-1-yl-2,4-dihydroxy-N-(3-hydroxy-5-methoxybenzyl)benzamide.

4. A composition comprising the compound, the isomer thereof, the pharmaceutically acceptable salt thereof, the prodrug thereof, the hydrate thereof or the solvate thereof according to claim 1.

5. The composition according to claim 4, wherein each of $R_1$, $R_3$ and $R_4$ is independently selected from a group consisting of hydrogen, hydroxy, $C_1$-$C_3$ alkoxy, $C_3$-$C_6$ cycloalkoxy, aryloxy and $C_1$-$C_3$ haloalkoxy;

$R_2$ is selected from a group consisting of hydrogen, $C_1$-$C_3$ alkyl, $C_3$-$C_6$ cycloalkyl, aryl and $C_1$-$C_3$ haloalkyl; and n is an integer selected from 1 to 3.

6. The composition according to claim 4, wherein the compound is selected from a group consisting of 5-adamantan-1-yl-N-[2-(3,4-dihydroxyphenyl)-ethyl]-2,4-dihydroxybenzamide, 5-adamantan-1-yl-N-[2-(3,4-dihydroxyphenyl)-ethyl]-2-hydroxy-4-methoxybenzamide, 5-adamantan-1-yl-N-(3,4-dihydroxybenzyl)-2,4-dihydroxybenzamide, 5-adamantan-1-yl-N-(3,4-dihydroxybenzyl)-2-hydroxy-4-methoxybenzamide, 5-adamantan-1-yl-2,4-dihydroxy-N-[2-(4-hydroxyphenyl)-ethyl]benzamide, 5-adamantan-1-yl-2-hydroxy-N-[2-(4-hydroxyphenyl)-ethyl]-4-methoxybenzamide, 5-adamantan-1-yl-N-[2-(4-hydroxyphenyl)-ethyl]-2,4-dimethoxybenzamide, 5-adamantan-1-yl-N-(2,4-dihydroxybenzyl)-2,4-dihydroxybenzamide, 5-adamantan-1-yl-N-(2,4-dihydroxybenzyl)-2-hydroxy-4-methoxybenzamide, 5-adamantan-1-yl-N-(2,4-dihydroxybenzyl)-2,4-dimethoxybenzamide, 3-adamantan-1-yl-N-(3,4-dihydroxybenzyl)-4-hydroxybenzamide, 3-adamantan-1-yl-N-(3,4-dihydroxybenzyl)-4-methoxybenzamide, 3-adamantan-1-yl-N-[2-(3,4-dihydroxyphenyl)-ethyl]-4-hydroxybenzamide, 3-adamantan-1-yl-N-[2-(3,4-dihydroxyphenyl)-ethyl]-4-methoxybenzamide, 3-adamantan-1-yl-4-hydroxy-N-[2-(4-hydroxyphenyl)-ethyl]benzamide, 3-adamantan-1-yl-N-[2-(4-hydroxyphenyl)-ethyl]-4-methoxybenzamide, 3-adamantan-1-yl-N-(2,4-dihydroxybenzyl)-4-hydroxybenzamide, 3-adamantan-1-yl-N-(2,4-dihydroxybenzyl)-4-methoxybenzamide, 5-adamantan-1-yl-N-(2,5-dimethoxybenzyl)-2,4-dihydroxybenzamide, 5-adamantan-1-yl-N-(2,5-dihydroxybenzyl)-2,4-dihydroxybenzamide, 5-adamantan-1-yl-N-(3,5-dimethoxybenzyl)-2,4-dihydroxybenzamide and 5-adamantan-1-yl-2,4-dihydroxy-N-(3-hydroxy-5-methoxybenzyl)benzamide.

7. The composition according to claim 4, which comprises the compound, the isomer thereof, the pharmaceutically acceptable salt thereof, the prodrug thereof, the hydrate thereof or the solvate thereof in an amount of 0.01-20 wt % based on the total weight of the composition.

8. The composition according to claim 4, which is a composition for external application to skin.

9. The composition according to claim 4, which is a cosmetic composition.

10. A method for improving skin whitening comprising administering an effective amount of the compound, the isomer thereof, the pharmaceutically acceptable salt thereof, the prodrug thereof, the hydrate thereof or the solvate thereof according to claim 1 to a subject in such need, wherein the method is for improving skin whitening.

11. The method according to claim 10, wherein each of $R_1$, $R_3$ and $R_4$ is independently selected from a group consisting of hydrogen, hydroxy, $C_1$-$C_3$ alkoxy, $C_3$-$C_6$ cycloalkoxy, aryloxy and $C_1$-$C_3$ haloalkoxy;

R$_2$ is selected from a group consisting of hydrogen, C$_1$-C$_3$ alkyl, C$_3$-C$_6$ cycloalkyl, aryl and C$_1$-C$_3$ haloalkyl; and n is an integer selected from 1 to 3.

12. The method according to claim 10,
wherein the compound is selected from a group consisting of 5-adamantan-1-yl-N-[2-(3,4-dihydroxyphenyl)-ethyl]-2,4-dihydroxybenzamide,
5-adamantan-1-yl-N-[2-(3,4-dihydroxyphenyl)-ethyl]-2-hydroxy-4-methoxybenzamide,
5-adamantan-1-yl-N-(3,4-dihydroxybenzyl)-2,4-dihydroxybenzamide,
5-adamantan-1-yl-N-(3,4-dihydroxybenzyl)-2-hydroxy-4-methoxybenzamide,
5-adamantan-1-yl-2,4-dihydroxy-N-[2-(4-hydroxyphenyl)-ethyl]benzamide,
5-adamantan-1-yl-2-hydroxy-N-[2-(4-hydroxyphenyl)-ethyl]-4-methoxybenzamide,
5-adamantan-1-yl-N-[2-(4-hydroxyphenyl)-ethyl]-2,4-dimethoxybenzamide,
5-adamantan-1-yl-N-(2,4-dihydroxybenzyl)-2,4-dihydroxybenzamide,
5-adamantan-1-yl-N-(2,4-dihydroxybenzyl)-2-hydroxy-4-methoxybenzamide,
5-adamantan-1-yl-N-(2,4-dihydroxybenzyl)-2,4-dimethoxybenzamide,
3-adamantan-1-yl-N-(3,4-dihydroxybenzyl)-4-hydroxybenzamide,
3-adamantan-1-yl-N-(3,4-dihydroxybenzyl)-4-methoxybenzamide,
3-adamantan-1-yl-N-[2-(3,4-dihydroxyphenyl)-ethyl]-4-hydroxybenzamide,
3-adamantan-1-yl-N-[2-(3,4-dihydroxyphenyl)-ethyl]-4-methoxybenzamide,
3-adamantan-1-yl-4-hydroxy-N-[2-(4-hydroxyphenyl)-ethyl]benzamide,
3-adamantan-1-yl-N-[2-(4-hydroxyphenyl)-ethyl]-4-methoxybenzamide,
3-adamantan-1-yl-N-(2,4-dihydroxybenzyl)-4-hydroxybenzamide,
3-adamantan-1-yl-N-(2,4-dihydroxybenzyl)-4-methoxybenzamide,
5-adamantan-1-yl-N-(2,5-dimethoxybenzyl)-2,4-dihydroxybenzamide,
5-adamantan-1-yl-N-(2,5-dihydroxybenzyl)-2,4-dihydroxybenzamide,
5-adamantan-1-yl-N-(3,5-dimethoxybenzyl)-2,4-dihydroxybenzamide and
5-adamantan-1-yl-2,4-dihydroxy-N-(3-hydroxy-5-methoxybenzyl)benzamide.

13. The method according to claim 10, wherein
the compound, the isomer thereof, the pharmaceutically acceptable salt thereof, the prodrug thereof, the hydrate thereof or the solvate thereof is administered in the form of a composition, and
the composition comprises the compound, the isomer thereof, the pharmaceutically acceptable salt thereof, the prodrug thereof, the hydrate thereof or the solvate thereof in an amount of 0.01-20 wt % based on the total weight of the composition.

* * * * *